US011478504B2

(12) United States Patent
Lynch et al.

(10) Patent No.: US 11,478,504 B2
(45) Date of Patent: *Oct. 25, 2022

(54) COMPOSITIONS AND METHODS FOR PREVENTING/TREATING METABOLIC SYNDROME (71) Applicant: INTERNATIONAL DEHYDRATED FOODS, INC., Springfield, MO (US)

(72) Inventors: Stephanie Lynch, Springfield, MO (US); Jack C. Cappozzo, Springfield, MO (US); Roger L. Dake, Springfield, MO (US)

(73) Assignee: INTERNATIONAL DEHYDRATED FOODS, INC., Springfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/832,413

(22) Filed: Mar. 27, 2020

(65) Prior Publication Data

US 2020/0230169 A1 Jul. 23, 2020

Related U.S. Application Data (63) Continuation-in-part of application No. 16/676,333, filed on Nov. 6, 2019, and a continuation of application No. PCT/US2018/053437, filed on Sep. 28, 2018, said application No. 16/676,333 is a continuation of application No. 14/325,694, filed on Jul. 8, 2014, now Pat. No. 10,555,967.

(60) Provisional application No. 62/564,406, filed on Sep. 28, 2017, provisional application No. 61/843,662, filed on Jul. 8, 2013.

(51) Int. Cl.
*A61K 31/737* (2006.01)
*A61K 35/57* (2015.01)
*A61K 31/401* (2006.01)
*A61K 31/4172* (2006.01)
*A61K 45/06* (2006.01)

(52) U.S. Cl.
CPC .......... *A61K 31/737* (2013.01); *A61K 31/401* (2013.01); *A61K 31/4172* (2013.01); *A61K 35/57* (2013.01); *A61K 45/06* (2013.01)

(58) Field of Classification Search
CPC ............... A61K 31/737; A61K 31/401; A61K 31/4172; A61K 35/57; A61K 45/06
See application file for complete search history.

(56) References Cited

U.S. PATENT DOCUMENTS

| | | | |
|---|---|---|---|
| 5,073,394 A | 12/1991 | Dake et al. | |
| 6,025,327 A | 2/2000 | Alkayali | |
| 6,323,319 B1 | 11/2001 | Alkayali | |
| 6,780,841 B2 * | 8/2004 | Ishaq | C12P 19/26 514/17.2 |
| 7,671,041 B2 | 3/2010 | Vouland et al. | |
| 8,288,356 B2 | 10/2012 | Obad et al. | |
| 8,481,072 B2 | 7/2013 | Minatelli et al. | |
| 8,507,757 B2 | 8/2013 | Minatelli et al. | |
| 8,524,980 B2 | 9/2013 | Minatelli et al. | |
| 8,557,275 B2 | 10/2013 | Minatelli et al. | |
| 8,679,551 B2 | 3/2014 | Ruff | |
| 8,927,032 B2 | 1/2015 | Ruff | |
| 8,945,608 B2 | 2/2015 | Minatelli et al. | |
| 8,962,924 B2 | 2/2015 | Minatelli et al. | |
| 8,999,373 B2 | 4/2015 | Minatelli et al. | |
| 9,028,814 B2 | 5/2015 | Minatelli et al. | |
| 9,034,366 B2 | 5/2015 | Minatelli et al. | |
| 9,050,364 B2 | 6/2015 | Minatelli et al. | |
| 9,216,164 B2 | 12/2015 | Minatelli et al. | |
| 9,238,043 B2 | 1/2016 | Minatelli et al. | |
| 10,555,967 B2 * | 2/2020 | Dake | A61P 3/10 |
| 10,694,767 B2 * | 6/2020 | Dake | A23L 23/00 |
| 10,694,768 B2 * | 6/2020 | Dake | A23J 1/02 |
| 10,757,957 B2 * | 9/2020 | Dake | A23L 2/66 |
| 2008/0096812 A1 | 4/2008 | Okamoto et al. | |
| 2014/0065205 A1 | 3/2014 | Anthony et al. | |
| 2015/0011500 A1 | 1/2015 | Dake et al. | |

FOREIGN PATENT DOCUMENTS

| | | | |
|---|---|---|---|
| JP | 4695846 B2 | 6/2011 | |
| MX | 2011012090 A | 5/2013 | |
| WO | 2011/145307 A1 | 11/2011 | |
| WO | 2012/170782 A2 | 12/2012 | |
| WO | WO 2016123053 A1 | 8/2016 | |

OTHER PUBLICATIONS

Extended European Search Report dated Feb. 9, 2017 for European Patent Application No. 14822469.4.
Connaughton (Nov. 2010), "From the Test Kitchen: Perfect Pressure Cooker Chicken Stock", Saveur, Nov. 8, 2010 (Nov. 8, 2010), pp. 1-3.
Du Souich et al. (Aug. 2009), "Immunomodulatory and anti-inflammatory effects of chondroitin sulphate", Journal of Cellular and Molecular Medicine, vol. 13, No. 8a, Aug. 1, 2009 (Aug. 1, 2009), pp. 1451-1463.
Sisson (Apr. 2010), "Mark's Daily Apple Cooking with Bones," Apr. 15, 2010 (Apr. 15, 2010 ), pp. 1-8.
Communication pursuant to Article 94(3) EPC dated Nov. 16, 2017 for European Patent Application No. 14822469.4 (8 pages).
Result of Formal Examination dated Mar. 22, 2016, for Colombian Patent Application No. 16-29211--2 (3 pages).

(Continued)

*Primary Examiner* — Jonathan S Lau
(74) *Attorney, Agent, or Firm* — Lathrop GPM LLP (57) ABSTRACT

Broth compositions prepared from poultry are disclosed. Selected poultry raw materials are processed to obtain a broth having high protein content. Certain specific amino acids and proteins are present at relatively higher concentration as compared to home-made broth. The disclosed broth compositions are effective in preventing and/or treating metabolic syndrome and may also provide other nutritional and health benefits.

9 Claims, 5 Drawing Sheets (56) References Cited

OTHER PUBLICATIONS

M.J. O'Neil et al., Merck Index, 14th Ed., Merck & Co. Whitehouse Station, NJ, 2006, only p. 368 supplied, see entry 2214.
Anon., Sigma Life Science, Products for Life Science Research, St. Louis, MO, 2008-2009, p. 475, see col. 1.
Sun et al. (2014) "Histidine supplementation alleviates inflammation in the adipose tissue of highfat diet-induced obese rats via the NF-kB- and PPARgamma-involved pathways", British Journal of Nutrition, vol. 112, pp. 477-185.
European Patent Application No. 18861957.1 Communication pursuant to Article 94(3) EPC, dated Feb. 18, 2022, 4 pages.
Amiot M. J. et al., "Effects of dietary polyphenols on metabolic syndrome features in humans: a systematic review", Obesity Reviews, vol. 17, No. 7, Jul. 1, 2016, pp. 573-586.
European Patent Application No. 18861957.1 extended European search report dated Feb. 19, 2021, 8 pages.
Hawkins et al.., Meeting abstract, "Inclusion of Chicken Broth AAC1 as a Dietary Supplement Modulates the Gut Microbiome: Results of Next-Generation DNA Sequencing", Database Biosis, Biosciences Information Service, Philadelphia, PA, US; Apr. 2016, 2 pages.
Durham et al., Meeting abstract "Biochemical Comparison of AAC1 Enriched Chicken Broth to Homemade Chicken Broth: Potential Benefits to Joint Health", Database Biosis, Biosciences Information Service, Philadelphia, PA, US; Apr. 2016.
Durham et al. Meeting abstract, "Chicken Broth AAC1 as a Dietary Supplement Inhibits Pain Transmission and Decreases Serum C-Reactive Protein Levels In a Model of TMJ Disorder", Database Biosis, Biosciences Information Service, Philadelphia, PA, US; Apr. 2016, 2 pages.
Parnell et al. "Prebiotic fiber modulation of the gut microbiota improves risk factors for obesity and the metabolic syndrome", Gut Microbes, vol. 3, No. 1, Jan. 1, 2012, pp. 29-34.
Lourdes Fernandez De Cossio et al., "Impact of prebiotics on metabolic and behavioral alterations in a mouse model of metabolic syndrome", Brain Behavior and Immunity vol. 64, Elsevier, Dec. 24, 2016pp. 33-49.

* cited by examiner

Figure 1

*Triglyceride Levels Obese Controls vs. Obese AAC1 vs. Obese Homemade4*

| Triglyceride Levels-SD (mg/dL) | | | |
|---|---|---|---|
| Group | Basal (mg/dL) | 12 Week (mg/dL) | Δ (mg/dL) |
| Obese (W) | 1060.8 ± 315.1 | 1346.5 ± 493.3* | 285.7 ± 696.7 |
| Obese (A) | 623.3 ± 103.6 | 1065.2 ± 332.7 | 441.9 ± 345.1 |
| Obese (H) | 710.5 ± 58.6 | 1061.0 ± 324.3+ | 350.5 ± 276.5 |

\* = Significant for Obese Control a $p < 0.025$, + = Significant from Basal at $p < 0.05$

Figure 2

*Cholesterol Levels Obese Controls vs. Obese AAC1 vs. Obese Homemade4*

| | HDL (mg/dL) ± SD | |
|---|---|---|
| Group | Basal | 12 Week |
| Obese (W) | 118.0 ± 39.3 | 212.5 ± 78.8 |
| Obese (A) | 90.4 ± 18.8 | 217.6 ± 84.2+ |
| Obese (H) | 127.2 ± 39.7 | 216.9 ± 72.3+ |

| | LDL (mg/dL) ± SD | |
|---|---|---|
| Group | Basal | 12 Week |
| Obese (W) | 17.8 ± 6.8 | 80.8 ± 7.5+ |
| Obese (A) | 38.3 ± 25.8 | 55.6 ± 37.7 |
| Obese (H) | 65.0 ± 61.4 | 97.3 ± 75.7+ |

| | Total (mg/dL) ± SD | |
|---|---|---|
| Group | Basal | 12 Week |
| Obese (W) | 161.1 ± 23.8 | 271.4 ± 62.7 |
| Obese (A) | 124.0 ± 35.6 | 264.1 ± 94.7+ |
| Obese (H) | 162.3 ± 65.7 | 317.5 ± 121.8+ |

| | Ratios (LDL/HDL) ± SD | |
|---|---|---|
| Group | Basal | 12 Week |
| Obese (W) | 0.15 ± 0.06 | 0.41 ± 0.12 |
| Obese (A) | 0.43 ± 0.25 | 0.26 ± 0.20+ |
| Obese (H) | 0.46 ± 0.37 | 0.44 ± 0.32 |

\* = Significant for Obese Control a $p < 0.025$, + = Significant from Basal at $p < 0.0$

COMPOSITIONS AND METHODS FOR PREVENTING/TREATING METABOLIC SYNDROME

RELATED APPLICATION

This application is a continuation application of International Patent Application No. PCT/US2018/053437 filed Sep. 28, 2018, which claims priority to U.S. Patent Application No. 62/564,406 filed Sep. 28, 2017. This application is also filed as a continuation-in-part of U.S. patent application Ser. No. 16/676,333 filed Nov. 6, 2019, which is a continuation of U.S. patent application Ser. No. 14/325,694, filed Jul. 8, 2014, now U.S. Pat. No. 10,555,967, which claims priority to U.S. Patent Application No. 61/843,662 filed Jul. 8, 2013. The entire contents of all the above-mentioned applications are hereby incorporated by reference into this application.

BACKGROUND

I. Field of Invention

This disclosure relates to a method of preventing and/or treating metabolic syndrome, or symptoms and conditions associated with metabolic syndrome. More particularly, it relates to medicament, pharmaceutical compositions, food, food ingredients or supplements, or nutraceutical ingredients or supplements useful for preventing or treating metabolic syndrome, or symptoms and conditions associated with metabolic syndrome.

II. Description of Related Art

Metabolic syndrome has been defined as certain conditions that increase the risk of developing atherosclerotic cardiovascular disease (CVD). These conditions include insulin resistance, obesity, atherogenic dyslipidemia and hypertension. These conditions vary in their measure but the categories have been published by several organizations such as the World Health Organization (WHO), the American Heart Association (AHA). See e.g., Huang, *Disease Models & Mechanisms* 2, 231-237 (2009). CVD or heart disease has been a primary focus but these conditions of metabolic syndrome have been associated with other diseases such as Type II diabetes, cognitive degeneration, gastrointestinal disorders, and immunological disorders (inflammation). A common occurrence of these diseases has been the association with oxidative stress that has overwhelmed the metabolism due to certain life styles. Western diet which is characterized by over-consumption of calories and rich in fat and carbohydrate, may contribute to development of metabolic syndrome.

SUMMARY

The present disclosure advances the art by providing broth compositions prepared from poultry and methods of preparing and using the same. In one embodiment, the disclosed compositions may help alleviate the symptoms associated with metabolic syndrome and may be used as an effective tool to control metabolic syndrome. In another embodiment, the disclosed compositions may be administered to a subject to lower the levels of Triglycerides in the blood of the subject. In another embodiment, the disclosed compositions may be administered to a subject to lower the levels of low-density lipoproteins (LDL) in the subject. In another embodiment, the disclosed compositions may be administered to a subject to increase the levels of high-density lipoproteins (HDL) in the subject. In another embodiment, the disclosed compositions may be administered to a subject to lower the ratio of LDL/HDL.

In one embodiment, the composition may be prepared from poultry, such as, for example, chicken, turkey, or other birds. In another embodiment, the disclosed composition may be prepared using parts from other animal sources. In another embodiment, the disclosed composition may be in the form of broth, stock, extract, or powder.

In one aspect, the broths disclosed herein may contain collagen, collagen peptides, meat protein and peptides, and various compounds such as chondroitin, which may improve GI health by exerting positive effects on microflora. These effects may improve conditions of metabolic syndrome by reducing oxidative stress. Collagen molecules are long molecules and are similar in length to other fiber molecules. In one aspect, these collagen fibers and peptides in the broths may have a positive effect on the microflora in the gut. In another aspect, these broths may help reduce LDL in animals. These effects of the broths may in turn help alleviate some of the symptoms of metabolic syndrome.

In one embodiment, the composition prepared according to the disclosed methods may have higher concentration of certain beneficial compounds. In another aspect, certain beneficial compounds may be enriched in the disclosed compositions to a greater extent as compared to other broth products currently available on the market. In another aspect, one or more ingredients may be supplemented in the broth to achieve certain health benefits that are not generally associated with chicken broth. Examples of such supplements may include but are not limited to ginger, coffee extract, ginseng, green tea, other botanicals such as willow bark or boswellia, curcumin/turmeric, omega-3 fatty acids, fish oil, krill oil, algal oil, Pycnogenol French maritime pine bark extract, grape seed extract, flax seed extract, ribonuclease, angiogenin, lactoferrin, ribonuclease-enriched lactoferrin, S-adenosyl methionine, collagen, collagen proteins or collagen peptides, gelatin, avocado/soybean unsaponifiables (ASU), extract of hops cones, egg shell membrane, polypeptides derived from milk, such as casein or whey, MSM (Methylsulfonylmethane), Yucca, Devils claw, Bromelain, glutamic acid, cocoa, stinging nettle, Vitamin E, Vitamin D3, walnut extract, etc. In one aspect, the disclosed broth may contain significant amount of collagen, collagen proteins and/or collagen peptides. In another aspect, significant amount of the collagen, collagen proteins and/or collagen peptides may be present naturally in the disclosed broth. In another aspect, significant amount of the collagen, collagen proteins and/or collagen peptides may be added into the disclosed broth as a supplement.

In home-style cooking, chicken or turkey broths may be made by cooking for extended period of time in an open vessel or under high temperature in a pressurized vessel. By contrast, this disclosure provides broth products having unique composition and methods of preparing the same. Also disclosed here are methods of selecting and preparing raw materials, cooking raw materials, and separating and purifying the resultant broths.

In one embodiment, raw materials from poultry or other animal sources may be comminuted to a great extent to maximize extraction of various beneficial compounds. In one aspect, the raw materials may be reduced to a size of less than about 2 cm, 1 cm, 5 mm, 4 mm, 3 mm, 2 mm, or less than 2 mm. Mechanical processing of the poultry parts to small sized particles prior to cooking may help maximizing extraction of certain compounds. In another embodiment, because the poultry parts have been mechanically processed to very small-sized particles prior to cooking, more gentle cooking condition (e.g., at a temperature of 60-100° C.) and shorter cooking time (from about 8 minutes to 300 minutes) may be used to obtain the broth from the processed poultry parts. Such gentler and shorter cooking may help prevent inactivation of certain compounds that would be otherwise inactivated if conventional processing and cooking methods are used. Preservation of such compounds may explain the superior health benefits observed when the disclosed broths are tested against other broth products that are not prepared according to the instantly disclosed methods.

In another embodiment, poultry parts with bones and cartilage may be mechanically separated and comminuted to fine pieces of less than 5 mm (millimeter), 4 mm, 3 mm, 2 mm, or 1 mm in size. In one aspect, no steps are taken to remove the residual meat from the bones. These small pieces may be cooked at about 70° C., 100° C., 110° C., 120° C., or as high as 150° C., for at least 8 minutes, 15 minutes, 30 minutes, 1 hour, 2 hours, 3 hours, or 6 hours or longer to maximize the extraction of certain broth fraction and/or compounds.

In another embodiment, the broth prepared according to the disclosed methods show different protein profiles from those obtained from other commercial broth products when analyzed by SDS-PAGE. In one aspect, at least 10%, 20%, 30%, 40%, 50%, 70%, or 90% of the total proteins in the disclosed compositions have a molecular weight of between 10 kD (kilo-Dalton) and 70 kD. In another aspect, at least 95% of the proteins in the disclosed compositions have a molecular weight of less than 100 kD. In another aspect, the methods may be used to further reduce molecular weight of the proteins in the broth to less than 10 kD, 5 kD, or even lower than 3 KD to enhance assimilation by a subject. By way of example, one or more enzymes that digest proteins may be used to reduce the molecular weight of the proteins in the broth.

In another embodiment, the disclosed composition may contain the amino acids proline and histidine, wherein the ratio between proline and histidine is at least 4:1 by weight. In one aspect, the proline is present in the composition by at least 8% (w/w), 10% or greater on solid basis. In another aspect, the ratio between the proline and the histidine is at least 6:1 by weight.

In another embodiment, the disclosed composition may contain the amino acids glycine and histidine, wherein the ratio between the glycine and histidine is at least 6:1 by weight. In one aspect, the glycine is present in the composition by at least 12%, 14% or greater (w/w) on solid basis. In another aspect, the ratio between the glycine and the histidine is at least 10:1 by weight.

In another embodiment, the disclosed composition may contain the amino acids hydroxyproline and histidine, wherein the ratio between the hydroxyproline and histidine is at least 4:1 by weight. In one aspect, the hydroxyproline is present in the composition by at least 7%, 8% or greater (w/w) on solid basis. In another aspect, the ratio between the hydroxyproline and the histidine is at least 6:1 by weight.

In another embodiment, the disclosed composition may contain proline, glycine, hydroxyproline and histidine. In one aspect, the ratio between the glycine and the histidine is at least 6:1 by weight. In another aspect, the glycine is present in the composition by at least 12% (w/w) on solid basis. In another aspect, the ratio between the proline and the histidine is at least 4:1 by weight. In another aspect, the ratio between the hydroxyproline and the histidine is at least 6:1 by weight.

In another embodiment, the disclosed composition may contain proline and other amino acids, and the amount of the proline is at least 10% by weight of the total amino acids in the composition. In another embodiment, the disclosed composition may contain glycine and other amino acids, and the amount of the glycine is at least 20% by weight of the total amino acids in the composition. In another embodiment, the disclosed composition may contain hydroxyproline and other amino acids, and the amount of the hydroxyproline is at least 8% by weight of the total amino acids in the composition.

In another embodiment, the disclosed composition may contain one or more branched chain amino acids (BCAA) (e.g., valine, leucine and isoleucine), and the BCAAs in the composition are present at a higher level than the level of BCAAs in other broth products. In one aspect, the amount of total BCAAs, including valine, leucine and isoleucine, is at least 5%, 6%, or 7% by weight of total amino acids in the composition.

In another embodiment, the broth products prepared according to this disclosure may have a moisture protein ratio (MPR) of between 999:1 and 1:999, or between 200:1 and 10:1. By way of example, a MPR of 200:1 means the product contains 200 parts water and 1 part meat (protein). In another embodiment, the broth products prepared according to this disclosure may have a moisture protein ratio (MPR) of between 150:1 and 40:1, or between 135:1 and 67:1.

Chondroitin sulfate (CS) is rich in cartilage and has been reported to be beneficial for joint health. The selection of raw materials and the process by which the broth is prepared may contribute to the relatively higher levels of chondroitin sulfate in the disclosed composition. In one embodiment of the present disclosure, the broth composition may contain at least 4%, 5%, 6%, 7%, 8%, or 10% of chondroitin sulfate by weight of total dry solids in the composition, as measured by using enzymatic digestion and LC-UV detection assay. See e.g., Ji et al., Journal of AOAC International, Vol. 90, No. 3, 659-69 (2007), which is hereby incorporated by reference into this disclosure.

In one aspect, the composition may be in a liquid form ready to be consumed or it may be in a concentrated liquid form such as a stock. In another aspect, the composition may be in a solid form, such as a powder or a paste.

In one embodiment, the composition may contain one or more polyphenols, wherein the concentration of the polyphenols is at least 4,000 µg/ml GAE (Gallic Acid Equivalent) based on Folin-Ciocalteu assay.

The broths disclosed herein may be characterized by the unique chemical composition as described above. The broths may also be characterized by the methods through which they are prepared. Moreover, the disclosed broths are also unique in the health benefits they may provide to a subject. Subjects may be divided into two groups, one group ingests (or consumes) an effective amount of the disclosed broth product each day, while the other group ingests water, or other broth products. The various indicators may then be measured and compared between the two groups.

In one embodiment, the composition disclosed herein may help prevent or treat metabolic syndrome or a symptom or condition associated with metabolic syndrome when administered to an individual as disclosed herein.

In another embodiment, the composition disclosed herein may reduce pain significantly in a subject when it is administered to the subject as compared to a subject not administered the composition.

For purpose of this disclosure, "significantly" means the observed difference between the treatment group and the control group is statistically significant.

Protein Kinase A (PKA) is a family of cyclic AMP (cAMP) dependent enzymes implicated in inflammation. In another embodiment, the composition may significantly reduce stress-induced expression of protein kinase A (PKA) in a subject administered said composition as compared to a control subject not administered said composition. In one aspect, the composition reduces expression of protein kinase A (PKA) by 20%, 30%, by 50% or greater in a subject administered said composition as compared to a control subject not administered said composition.

In another embodiment, the disclosed compositions may substantially inhibit activity of cyclooxygenase (COX)-2 as measured by using a COX Inhibitor Screening Assay. In one aspect, the inhibition of COX-2 is greater than 20%, 30%, or 40%, as compared with subject with no administration of the composition. In another aspect, the disclosed composition causes no significant inhibition of COX1 as measured by using a COX Inhibitor Screening Assay. In another aspect, the ratio of inhibition between COX2 and COX1, i.e., COX2/COX1 exerted by the instant composition is between 2 and 30, between 5 and 20, or between 10 and 20.

In one embodiment, it is provided here methods for preventing or treating various diseases by administering to a subject an effective amount of a composition prepared according to the instant disclosure. In another embodiment, the disclosed methods may further include a step of identifying subjects who are in need of treatments. In one aspect, the subject may be susceptible to one or more of the diseases. In another aspect, the subject may already have one or more of the diseases. Examples of the diseases may include but are not limited to joint disease, inflammation, autoimmune disease, diabetes, metabolic disorder, cognitive disorder and combination thereof.

In one aspect, the effective amount may be an amount of the composition that significantly reduces stress-induced expression of protein kinase A (PKA) as compared to a control subject who has not been administered the composition. In another aspect, the composition may reduce expression of the protein kinase A (PKA) by at least 50% in a subject administered the composition as compared to a control subject who has not been administered an effective amount of the composition.

In another aspect, the effective amount may be an amount of the composition that inhibits COX-2 activity by at least 20% in the subject while not significantly inhibiting COX1 activity. In another aspect, the ratio of inhibition between COX2 and COX1 exerted by the composition is between 2 and 30.

In another aspect, the effective amount is an amount of the composition that significantly reduces nociception (pain) as compared to a control subject who has not been administered an effective amount of the composition.

DETAILED DESCRIPTION

Chicken soup and chicken broth have been available for human consumption for centuries. Many studies have been performed that show various health benefits of chicken soup or broth. According to conventional home-style method, chicken soup or broth is prepared by boiling whole chicken or large chicken parts in a pot of water for an extended period of time. The soup or broth prepared according to this method may not have maximized the health promoting effects of the soup or broth because some of the compounds may have been lost during cooking or during processing, while other compounds may not have been extracted from the chicken parts.

The present disclosure provides an improved method by processing chicken parts prior to cooking and by controlling the processing temperature and cooking time to maximize the extraction of beneficial compounds while, concomitantly, minimizing loss of activity due to harsh processing conditions.

Specially selected raw materials from poultry are processed according to the disclosed methods to obtain a broth having high protein content. Certain amino acids are present in relatively higher concentration as compared to a homemade broth or other commercial products. As shown in various animal studies described herein, the disclosed broth compositions may prove effective in preventing and/or treating joint diseases and the underlying pathology. The compositions may also provide other nutritional and health benefits such as decreasing inflammation.

The terms "broth" and "soup" refer to a liquid composition containing at least one solute and may also be used to refer to a ready to serve form, a concentrate, a stock in either liquid or solid form.

The poultry broth of the disclosure may contain a significant amount of different amino acids. Such amino acids may be present in the form of a protein or as free amino acids in the broth. Total amino acids include both amino acids present in the form of proteins and those present as free amino acids. For purpose of this disclosure, the ratio of different amino acids in a broth composition refers to the ratio between total amino acids.

The term "dry solid" or "solid" as used herein refers to the components of a liquid composition that remain after all free liquid is removed from the liquid composition. In the case of an aqueous broth, the free liquid is water.

The term "administer" means delivering of a material to an individual, such as by oral ingestion.

The term "subject" or "individual" is used to refer to a mammal, including human being.

The term "substantially" means by at least 10-20%.

The following items describe some of the embodiments of the present disclosure:

Item 1. A pharmaceutical composition comprising an effective amount of a broth prepared from poultry parts, said pharmaceutical composition comprising proline and histidine derived from said poultry parts, wherein said proline and histidine are present in said pharmaceutical composition at a ratio between proline and histidine of at least 4:1 by weight, and wherein said effective amount is an amount of the broth effective in preventing or treating metabolic syndrome or a symptom or condition associated with metabolic syndrome.

Item 2. The pharmaceutical composition of Item 1, wherein said effective amount of the composition is an amount effective in reducing/alleviating at least one symptom of the metabolic syndrome, said at least one symptom being selected from the group consisting of a) proinflammatory or inflammation state, b) joint pain, c) diminishing cognition, d) increased BMI, e) gut dysbiosis, f) hypertension, and (g) high cholesterol.

Item 3. The pharmaceutical composition of Item 1, wherein said effective amount of the composition is an amount effective in reducing/alleviating two or more symptoms of the metabolic syndrome, said two or more symptoms being selected from the group consisting of i) proinflammatory or inflammation state, ii) joint pain, iii) diminishing cognition, iv) increased BMI, v) gut dysbiosis, vi) hypertension vii) high serum lipids, viii) pain, ix) insulin resistance with or without glucose intolerance, and (x) high cholesterol.

Item 4. The pharmaceutical composition of any of the preceding Items, wherein said effective amount of the composition is an amount effective in reducing COX-2 activity while not affecting activity of COX-1 in the individual.

Item 5. The pharmaceutical composition of any of the preceding Items, wherein said pharmaceutical composition comprises an enhanced level of chondroitin sulfate derived from said poultry parts, said enhanced level of chondroitin sulfate being at least 4% by weight of total dry solids of the composition.

Item 6. A method of preventing or treating metabolic syndrome in an individual, comprising administering to the individual an effective amount of a composition prepared from poultry parts, said composition comprising proline and histidine derived from said poultry parts, wherein said proline and histidine are present in said pharmaceutical composition at a ratio between proline and histidine of at least 4:1 by weight, and wherein said effective amount is an amount of the composition effective in preventing or treating metabolic syndrome or a symptom or condition associated with metabolic syndrome.

Item 7. The method composition of Item 6, wherein said composition comprises an enhanced level of chondroitin sulfate derived from said poultry parts, said enhanced level of chondroitin sulfate being at least 4% by weight of total dry solids of the composition.

Item 8. The method of Item 6, wherein said effective amount of the composition is an amount effective in reducing/alleviating at least one symptom of the metabolic syndrome, said at least one symptom being selected from the group consisting of a) proinflammatory or inflammation state, b) joint pain, c) diminishing cognition, d) increased BMI, e) gut dysbiosis, f) hypertension, and (g) high cholesterol.

Item 9. The method of Item 6, wherein said effective amount of the composition is an amount effective in reducing/alleviating two or more symptoms of the metabolic syndrome, said two or more symptoms being selected from the group consisting of i) proinflammatory or inflammation state, ii) joint pain, iii) diminishing cognition, iv) increased BMI, v) gut dysbiosis, vi) hypertension vii) high serum lipids, viii) pain, ix) insulin resistance with or without glucose intolerance, and (x) high cholesterol.

Item 10. The method of Item 6, wherein said effective amount of the composition is an amount effective in reducing/alleviating three or more symptoms of the metabolic syndrome, said three or more symptoms being selected from the group consisting of i) proinflammatory or inflammation state, ii) joint pain, iii) diminishing cognition, iv) increased BMI, v) gut dysbiosis, vi) hypertension vii) increased serum lipids, viii) pain, ix) insulin resistance with or without glucose intolerance, and (x) high cholesterol.

Item 11. The method of any of Items 6-10, wherein said effective amount of the composition is an amount effective in reducing COX-2 activity while not affecting activity of COX-1 in the individual.

Item 12. The method of any of Items 6-11, wherein said effective amount of the composition is an amount effective in reducing the level of expression or concentration of C-Reactive protein, or protein kinase A (PKA) in the individual.

Item 13. The method of any of Items 6-12, wherein said effective amount of the composition is an amount effective in reducing the amount of adiponectin in the individual.

Item 14. The method of any of Items 6-13, wherein said effective amount of the composition is an amount effective in reducing low density lipoproteins (LDL) in the individual.

Item 15. The method of any of Items 6-14, wherein said effective amount of the composition is an amount effective in lowering ratio between low density lipoproteins (LDL) and high density lipoproteins (HDL) (LDL/HDL) in the individual.

Item 16. The method of any of Items 6-15, wherein at least 1 mg of said composition per pound of body weight of the individual is administered to the individual per day.

Item 17. The method of any of Items 6-15, wherein between 1-100 mg of said composition per pound of body weight of the individual is administered to the individual per day.

Item 18. The method of any of Items 6-17, wherein said composition is administered to the individual in a form selected from the group consisting of a medicament, a pharmaceutical composition, a food, a food ingredient, a supplement, and a nutraceutical ingredient.

EXAMPLES

The following examples are provided for purposes of illustration of the embodiments only and are not intended to be limiting. The raw materials, reagents, chemicals, and other materials are presented as exemplary components or reagents, and various modifications may be made in view of the foregoing discussion within the scope of this disclosure. Unless otherwise specified in this disclosure, components, reagents, protocol, and other methods used in the system and the assays, as described in the Examples, are for the purpose of illustration only.

Example 1 Preparation of Broth from Turkey Parts

In this example, turkey parts were used to prepare a broth and the overall quality and potential health benefits of the broth were determined. Briefly, raw turkey was mechanically separated and the parts were finely comminuted to less than 2 mm in size to maximize extraction. The small-sized parts from the turkey were gently cooked to 195° F. in steam for about 15 minutes or less. The broth was then separated from the insoluble fraction by decanting. Freed fat in the broth was also removed from the broth by a centrifugal separator. The broth was concentrated in a commercial evaporator, chilled, and packaged for sale.

Example 2 Preparation of Broth from Chicken Parts

In this study, chopped chicken parts containing chicken bones and cartilage were cooked in water at a temperature greater than 250° F. for more than 6 hours to maximize the extraction of certain broth fraction and/or compounds. The broth obtained from this process was designated "AAC1" for internal reference. More particularly, USDA inspected chopped raw chicken bones remaining after major muscles were removed were cooked in water in a large commercial stainless steel cooking tank. After cooking, the liquid broth portion was separated from the chicken solids by decanting. The broth was concentrated in a commercial evaporator then spray dried and packed in labeled containers.

Example 3 Comparing the Protein and Amino Acid Profiles of Different Broths

Proteins are large molecules composed of one or more chains of amino acids that perform a wide array of functions in biological systems including, for example, functioning as enzymes, facilitating cell communication, and providing structural support to cells. Humans, as well as other animals, obtain essential amino acids from protein consumed as part of their diet since they lack enzymes needed to synthesize them. Ingestion of proteins leads to their break down into amino acids through the digestive process. The amino acids can then be used in protein biosynthesis in muscle production and maintenance, glucose production, serve as a dietary nitrogen source, and serve as a fuel source if necessary. The objective of this study was to determine the concentration and size range of proteins in chicken broth AAC1 as compared to a home-made product.

One sample prepared according to this disclosure (AAC1) and another sample prepared according to home-style cooking methods (Homemade) were compared. The percent solid (w/v) for AAC1 was 8% solid, while the percentage (w/v) for Homemade was 1.7% solid.

Prior to determining the amount of protein by the Bradford method, each sample was diluted in distilled water to a final 1% w/v solution. A standard curve was prepared using bovine serum albumin (0-3.5 µg/µL). All samples were analyzed in triplicate. The amount of total protein was determined using a plate reader at a wavelength of 595 nm. Results are shown in Table 1.

TABLE 1

Amount of total protein in broth samples

| Sample | Values | Results | Mean Results | Concentration | SD | CV |
|---|---|---|---|---|---|---|
| AAC1 | 0.446 | 1.558 | 1.691 | 1.691 | 0.132 | 7.8 |
|  | 0.461 | 1.693 |  |  |  |  |
|  | 0.474 | 1.821 |  |  |  |  |
| Homemade | 0.544 | 2.496 | 2.52 | 2.52 | 0.034 | 1.3 |
|  | 0.549 | 2.544 |  |  |  |  |

To correct for differences in the percent solids in AAC1 (8%) and Homemade (1.7%) samples, the protein values based on a 1% solution for AAC1 and Homemade were multiplied by their respective starting % solids. The final adjusted amount of total protein for AAC1 and Homemade are shown in Table 2.

TABLE 2

Adjusted total protein concentration in AAC1 and homemade broth

| Sample | Adjusted Final Concentration | % of AAC1 |
|---|---|---|
| AAC1 | 13.6 µg/ul | — |
| Homemade | 4.3 µg/ul | 31.6% |

To determine the protein profile of each sample, equal volumes of the AAC1 and Homemade samples (15.6 µl) were each mixed with Laemmli's sample buffer and a reducing agent, heated at 95° C. for 5 minutes, and separated on a 4-12% Bis Tris gel. The relative size range of the proteins was determined by comparison to a commercially available protein standard (ranging from 4.5 kDa to 300 kDa). A constant voltage of 150V was applied to the gel for 30 minutes, allowing for separation of proteins in each sample. The proteins were visualized in the gel using SimplyBlue™ SafeStain.

Figure 1:
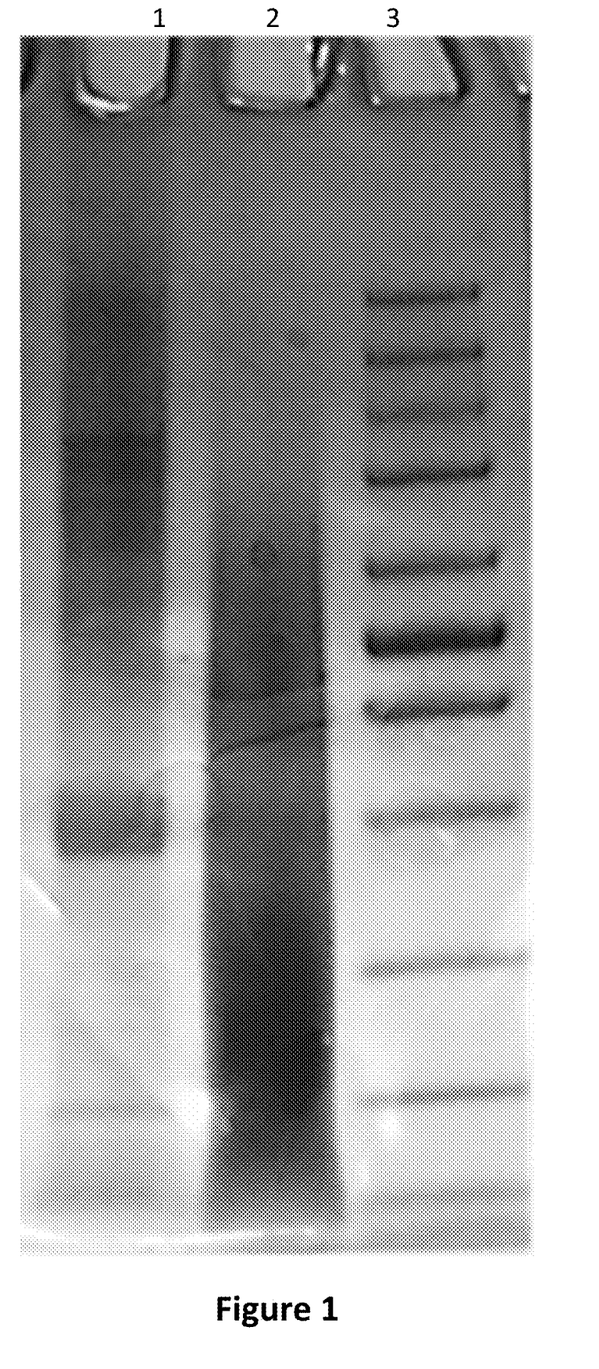
FIG. 1 shows the protein profile by staining of proteins separated by SDS-PAGE.

The results are shown in FIG. 1. Lane 1 shows the protein profile for homemade broth, lane 2 for the AAC1 broth, and lane 3 is molecular weight standard. Based on the protein profiles, AAC1 is composed of approximately 3 times more protein than a homemade product. Proteins in the homemade product displayed a wider range of molecular weight distribution, containing both large (up to about 300-500 kD) and small proteins (about 5-15kD). By contrast, the majority (i.e., greater than 50%) of proteins in AAC1 has molecular weight of between 70 kDa and 15 kDa.

Individual amino acid content was also analyzed. Table 3 below shows the individual amino acid content of the broth compositions prepared according to the disclosed methods as compared to those prepared using home-style methods as well as other commercial products.

TABLE 3

Amino acid composition of different broths

| Table Two: Content values above calculated to 100% solids basis: | 3823 W/W% | Commercial product % | Home-made-1 | Home-made-2 | AAC1-1 | AAC1-2 | AAC1-3 |
|---|---|---|---|---|---|---|---|
| TAURINE | 2.50 |  |  |  |  |  |  |
| ASPARTIC ACID | 3.63 | 2.44 | 3.63 | 3.47 | 7.04 | 5.34 | 5.38 |
| THREONINE | 1.44 | 0.76 | 1.52 | 1.42 | 1.75 | 2.13 | 1.79 |
| SERINE | 1.56 | 1.34 | 1.96 | 1.89 | 2.08 | 1.88 | 2.40 |
| GLUTAMIC ACID | 10.25 | 6.98 | 9.44 | 9.26 | 10.52 | 9.50 | 10.14 |
| PROLINE | 3.53 | 3.05 | 5.93 | 5.57 | 9.59 | 10.66 | 11.07 |
| HYDROXYPROLINE | 2.19 | 2.99 | 5.31 | 4.92 | na | 7.00 | 9.39 |

TABLE 3-continued

Amino acid composition of different broths

Table Two: Content values above calculated to 100% solids basis:

| | 3823 W/W% | Commercial product % | Home-made-1 | Home-made-2 | AAC1-1 | AAC1-2 | AAC1-3 |
|---|---|---|---|---|---|---|---|
| GLYCINE | 5.97 | 7.38 | 8.79 | 9.47 | 18.02 | 15.41 | 17.68 |
| Lanthionine | 0.06 | 0.00 | 0.00 | 0.00 | 0.00 | 0.00 | 0.00 |
| ALANINE | 3.91 | 3.37 | 4.60 | 4.58 | 8.06 | 7.53 | 7.53 |
| CYSTINE | 0.44 | 0.29 | 0.34 | 0.40 | 0.00 | 0.25 | 0.17 |
| VALINE | 1.44 | 0.73 | 1.43 | 1.42 | 2.44 | 2.19 | 2.21 |
| ISOLEUCINE | 1.13 | 0.47 | 1.18 | 1.02 | 1.54 | 1.59 | 1.59 |
| LEUCINE | 2.72 | 1.51 | 2.48 | 2.32 | 3.38 | 3.47 | 3.43 |
| METHIONINE | 0.81 | 0.52 | 0.93 | 0.77 | 1.01 | 1.06 | 1.10 |
| TYROSINE | 0.88 | 0.44 | 0.81 | 0.65 | 1.09 | 1.00 | 0.90 |
| PHENYLALANINE | 1.00 | 0.73 | 9.53 | 7.03 | 2.30 | 2.16 | 1.98 |
| HYDROXYLYSINE | 0.16 | 0.00 | 0.00 | 0.00 | 0.00 | 0.00 | 0.00 |
| HISTIDINE | 2.03 | 2.56 | 2.70 | 1.73 | 1.32 | 1.16 | 1.00 |
| ORNITHINE | 2.25 | 0.00 | 0.00 | 0.00 | 0.00 | 0.00 | 0.00 |
| LYSINE | 3.75 | 2.67 | 3.07 | 3.00 | 3.96 | 3.66 | 3.05 |
| ARGININE | 3.06 | 2.79 | 4.01 | 3.75 | 8.24 | 6.69 | 6.61 |
| TRYTOPHAN | 0.16 | 0.06 | 0.12 | 0.09 | | 0.22 | 0.15 |
| Total | 54.84 | 41.08 | 67.80 | 62.79 | 82.35 | 82.88 | 87.55 |

Example 4 Comparing Levels of Chondroitin Sulfate (CS) in Different Broths

Chondroitin sulfate (CS) is an important structural compound found in cartilage and is implicated in joint health. CS has been shown to reduce the levels of many inflammatory mediators such as iNOS, PGE2, COX-2 (Gwendolyn, Spine 2011), and NFkB (Vallières, Osteoarthritis Cartilage, 2010). The goal of this study was to determine the amount of CS in various chicken broth samples. Chicken broths were analyzed for total CS using enzymatic digestion and LC-UV detection (Ji, Journal of AOAC International, 2007). Results were calculated as area on the curve compared to standard samples and the limit of quantification as 8 mg chondroitin sulfate/g dry material (Table 4). Among all chicken broths tested, AAC1 had the greatest amount of CS (8.797% w/w).

TABLE 4

Amounts of chondroitin sulfate (CS)

| Samples | Average (mg) | Dry mg/g | Dry % w/w |
|---|---|---|---|
| Powdered Chicken Broth AAC1 | 17.480 | 87.971 | 8.797 |
| Powdered Chicken Broth H814 | 15.443 | 67.553 | 6.755 |
| Frozen Concentrate TSN | 10.886 | 52.059 | 5.206 |
| Frozen Concentrate IDF Chicken 823 | 8.627 | 42.104 | 4.210 |
| Home Style Broth from Back Bones | 5.866 | 28.258 | 2.826 |
| Frozen Concentrate Turkey 824 | 5.243 | 26.227 | 2.623 |
| Powdered Chicken Broth HML 34511 | 4.979 | 24.335 | 2.434 |
| Powdered Chicken Broth A1004 | 3.817 | 18.305 | 1.830 |
| Powdered Chicken Broth P1301 | 3.075 | 15.054 | 1.505 |
| Home Style Broth from Chicken Parts | 2.185 | 10.99 | 1.09 |
| Home Style Broth from Chicken Necks | 1.937 | 9.361 | 0.936 |

Example 5 Comparison of Concentration of Polyphenols in Different Chicken Broths The concentration of polyphenols in different chicken broths was determined using a modified Folin-Ciocalteau method (Slinkard, American Journal of Enology and Viticulture, 1977). Polyphenols are a class of chemical compounds known to have anti-oxidant and anti-inflammatory properties. While both AAC1 and home-style broths contained polyphenols, AAC1 contained 4828.8 μg/mL GAE of polyphenols, which is approximately 7 times more GAE of polyphenols than a homemade broth (687.7 μg/mL GAE) made from the same kind of chicken parts.

Example 6 Effect of the Broth Composition on Metabolic Syndrome in Obese Rats and Lean Healthy Rats In this test, AAC1, Homemade4 (854.5 mg/kg/day and 312.3 mg/kg/day respectively) broth, or water control were fed to Obese rats or lean healthy rats and the effects were assessed.

There were many models used to study MS; however, the Zucker Fatty Rat appeared to be the preferred choice for this type of study. The Zucker Rat contains a genetic spontaneous autosomal recessive mutation on Chromosome 5. This mutation promotes the development of obesity by 5 weeks of age, and continues throughout their lives. As seen in human presentation of MS, as the obesity state develops, the animals present with hyperglycemia, mild glucose intolerance, hyperlipidemia, and moderate hypertension. In this study, we were working with a factorial design with repeated measures. Assuming that we were anticipating a medium effect size (f=0.20) were α=0.05 powered at 0.80, we anticipated the use of 48 animals (24 Zucker Lean, 24 Zucker) in order to suitably observe the effects detailed in this study. We looked for changes in 6 groups (Lean+Water, Lean+AAC1, Lean+Homemade, Obese+Water, Obese+AAC1, Obese+Homemade) allowing for an n=8 in each condition.

A total of 24 Zucker lean (cat #186) and 24 Zucker Obese (Cat #185) were purchased from Charles River Laboratories at 8 weeks of age and allowed to acclimate to the facility conditions for 1 week prior to initiation of studies. During this time, investigators handled the animals for 5 minutes each day to acclimate the animals to the investigators involved in this study. Once acclimated to facility conditions, animals were acclimated to blood pressure holding devises used in this study. Animals entered the study at the age of 10 weeks old.

Two chicken broths (ACC1 and Homemade 4) were used in this study. Broth ACC1 was made at a 1% (w/v) by placing 10 g of powdered broth in a clean, autoclaved bottle. The bottle was then filled to the 1 L mark with filtered water. Solutions for Homemade broth were made in a similar fashion. Broth was measured out into 125 mL increments and placed into clean bottles as previously described. The bottle was then filled to the 1 L mark with filtered water, leaving the final concentration 0.415% solid. All solutions were then placed in a warm, sonication bath for 30 minutes to allow all components of the broths to evenly go into solution. Broths were placed in the refrigerator until they were used. Animals that received broth diets were fed their assigned broth for a complete twelve weeks after initial baseline assessments prior to any additional testing. Bottles were changed three times a week in order to ensure fresh product was consumed and to avoid any bacterial contamination in the water bottles during feeding.

Figure 2:
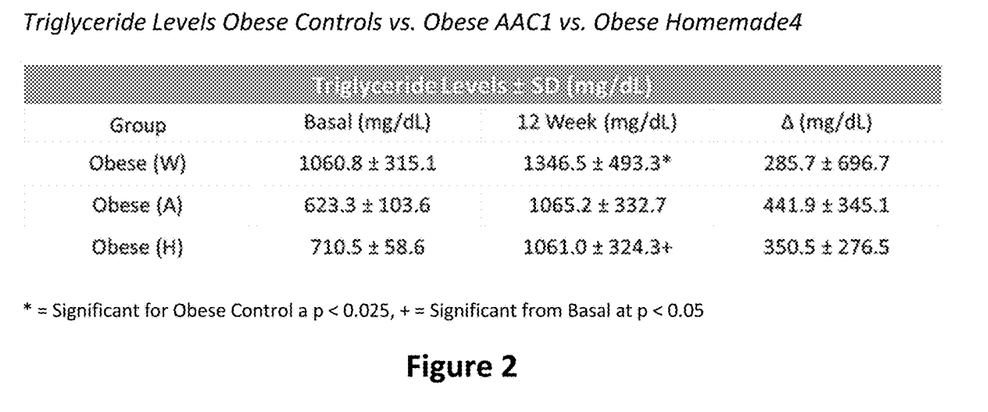
FIG. 2 shows the effect on triglyceride levels in Obese rats fed with the disclosed compositions as compared with controls.
Figure 3:
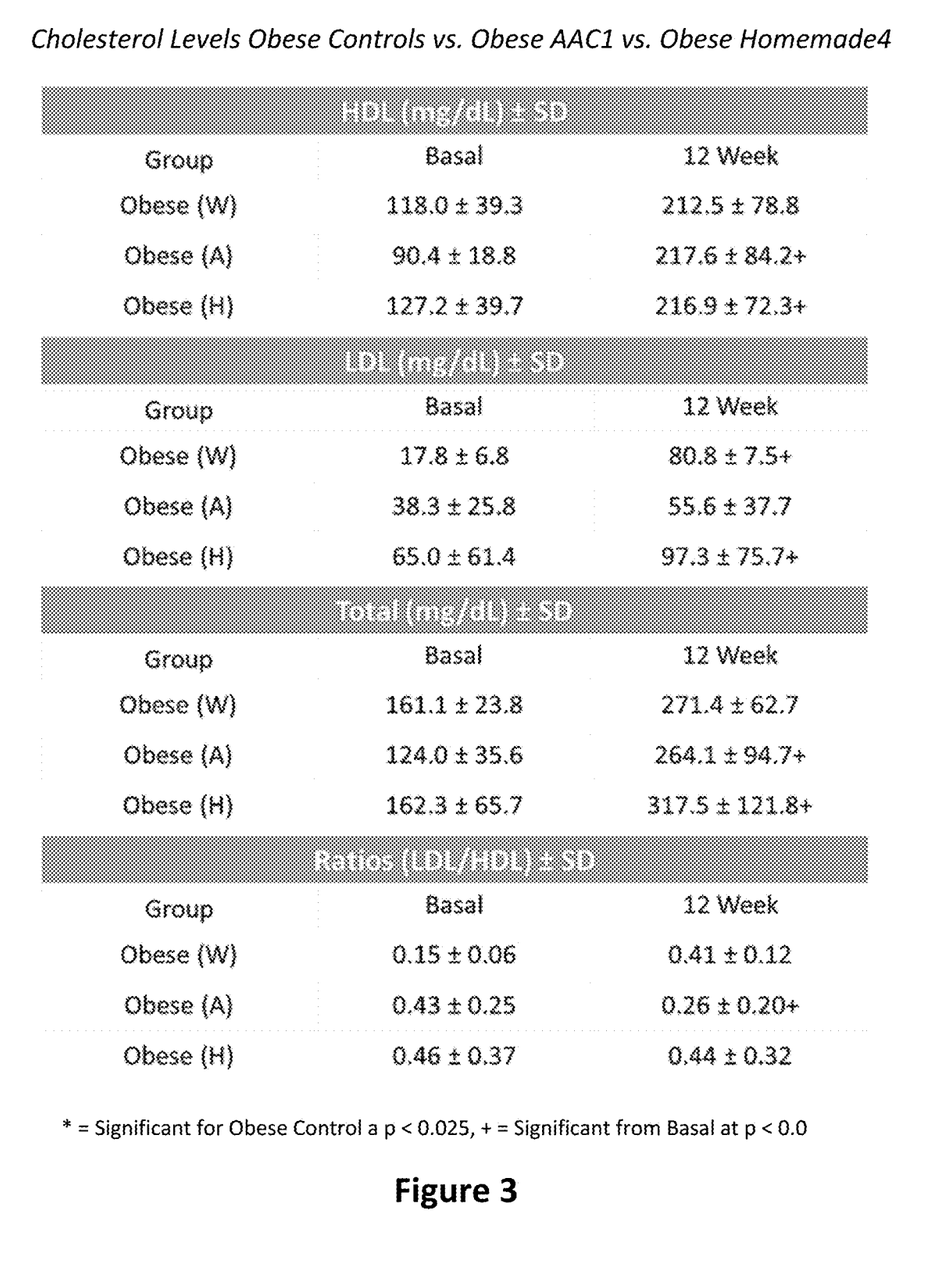
FIG. 3 shows the effect on cholesterol levels in Obese rats fed with the disclosed compositions as compared with controls.

While AAC1 or Homemade4 (H4) (854.5 mg/kg body weight/day and 312.3 mg/kg body weight/day respectively) broth did not seem to have a statistically significant effect on weight gain (Data not shown), Food Intake (Data not shown), Girth (Data not shown), Blood Pressure (Data not shown), or HbA1c (Data not shown), some trends were observed in Triglyceride (FIG. 2) and Cholesterol levels (FIG. 3). For example, Obese animals that were fed AAC1 showed reduced change in circulating Triglyceride levels as compared to both the Obese water group and Obese Homemade4 fed group. Note that considerable variations existed in these groups.

Although no significant increase in HDL levels were observed, significant differences existed with respect to LDL levels in the AAC1 group as compared to the control groups fed with water or H4 broth. These findings suggested that AAC1 broth lowered LDL levels, similar to the effect of statin drugs. Importantly, an improved (protective) change in the ratio of LDL to HDL in the Obese animals on the AAC1 diet was also observed as compared to the H4 or water controls.

Consumption of AAC1 or Homemade4 (883.3 mg/kg body weight/day and 327.8 mg/kg body weight/day, respectively) broth did not seem to cause a significant change in Lean healthy rats as compared to the control group fed with water alone. No differences in weight (Data not shown), food intake (Data not shown), Girth (Data not shown), Blood Pressure (Data not shown), or HbA1c (Data not shown) were observed. However, AAC1 appeared to lower the Triglycerides levels as compared to the control group fed with water alone (Data not shown). AAC1 also appeared to lower the LDL levels as compared to the control group fed with water alone (Data not shown). Note that considerable variations were observed in these groups.

Example 7 Effect of the Broth Composition on COX-2 Activity

The COX family of enzymes is responsible for the synthesis of prostanoids such as prostaglandins. COX-1 is constitutively active while COX-2 is inducible and hence is upregulated during inflammation and pain. Compounds that block COX-2 activation while not effecting COX-1 are of particular interest due to their ability to block inflammation while not causing unwanted side effects mediated by blocking COX-1 activity. The level and specificity of COX inhibition by the chicken broth prepared according to the disclosed methods was investigated.

Using an in vitro COX enzyme inhibitor assay (Abcam), chicken broth samples were assayed for their ability to block COX-1 and COX-2 activity according to the manufacturer's protocol. The results are shown in Table 5.

TABLE 5

Selective inhibition of COX-1 and COX-2

| Sample | Enzyme | % Inhibition | Ratio of COX2/COX1 Inhibition |
| --- | --- | --- | --- |
| Powdered IDF AAC1 | COX-1 | -2.3 | 18.34 |
|  | COX-2 | 42.4 |  |
| Frozen IDF 823 | COX-1 | -51.5 | 0.43 |
|  | COX-2 | 22.1 |  |
| Home Style Broth from Back Bones | COX-1 | -17.9 | 1.57 |
|  | COX-2 | 28.1 |  |
| Home Style Broth from Necks | COX-1 | -32.5 | 0.78 |
|  | COX-2 | 25.3 |  |
| IDF Turkey 824 | COX-1 | -21.7 | 1.51 |
|  | COX-2 | 32.7 |  |
| Chicken Broth K | COX-1 | -25.5 | 1.21 |
|  | COX-2 | 30.8 |  |
| Commercial Broth TSN | COX-1 | -5.1 | 5.16 |
|  | COX-2 | 26.3 |  |
| Commercial Broth H814 | COX-1 | -39.9 | 0.28 |
|  | COX-2 | 11.3 |  |
| Commercial Broth A1004 | COX-1 | -9.2 | 4.01 |
|  | COX-2 | 36.7 |  |
| Commercial Broth HML | COX-1 | -27.0 | 1.01 |
|  | COX-2 | 27.3 |  |
| Commercial Broth PLNT | COX-1 | -19.9 | 2.36 |
|  | COX-2 | 47.1 |  |
| Home Style Broth from same raw parts | COX-1 | -5.2 | 0.67 |
|  | COX-2 | 3.5 |  |

Broth labeled "Home Style Broth from same raw parts" was a broth prepared using traditional home-style cooking method with the same raw materials as those used for preparing AAC1. As shown in Table 5 above, chicken broth AAC1 showed the greatest ratio of COX-2 inhibition to COX-1 inhibition (18.34) with greater than 40% inhibition of COX-2 enzyme activity as compared to other commercial products or "Home Style Broth from same raw parts."

Example 8 Effect of the Disclosed Broth on Joint Diseases by Regulating Protein Kinase A Temporomandibular Joint Disorder (TMD) is a disease affecting the temporomandibular or jaw joint (TMJ), the muscles of mastication, or both. TMD is believed to be caused by activation of neurons and glia cells located in the trigeminal system (Tjakkes et al., 2010). The prevalence of TMD symptoms have been reported in up to 93% in the general population with varying incidence rates (Zhao et al., 2011). Further development of TMD may also lead to the development of a chronically sensitized state of the disorder.

Protein kinase A (PKA) is a member of the family of cyclic AMP (cAMP) dependent enzymes that act as pro-inflammatory molecules in peripheral and central nervous systems. Increased levels of PKA expression by sensory nociceptive neurons has been reported during the chronic sensitized state. The objective of this study was to study the effects of commercially available broths, home-style broths, and the broths according to the instant disclosure. These various products may contain certain anti-inflammatory molecules that have some effects on TMD. These molecules may exert their effects through PKA in regulating the development and progress of TMD.

Three chicken broths (AAC1, TSN, and a homemade broth) were investigated in this study. Broth AAC1 (8% solids) was prepared at a concentration of 0.5% (w/v). First, 5 g of powdered broth was placed in a clean, autoclaved bottle. The bottle was then filled to the 1 L mark with filtered water and the mixture was stirred to allow the powder to dissolve in water. A homemade style broth (1.7%) was also tested as a control. To achieve a dosage that would allow for the comparison of AAC1 and the homemade-style broth, the homemade broth was diluted 16 fold with filtered water by placing 62.5 mL of stock broth and diluting the broth to 1 L. A commercially available broth, TSN, was also tested as another control. To ensure TSN was tested at a concentration similar to that of AAC1, the solution for TSN (33.3% solid) was made in a similar manner. The TSN broth was allowed to warm until a consistency of the stock broth was non-gelatinous. Broths were measured out into 16.7 g increments and placed into clean bottles as previously described. The bottle was then filled to the 1 L mark with filtered water. All solutions were then placed in a warm, sonication bath for 30 minutes to allow all components of the broths to be evenly solubilized. Broths were stored in the refrigerator until they were administered to the animals via water bottle administration for 2 weeks prior to TMD induction.

Adult Sprague-Dawley male rats (200 g-300 g) were used in this study. The rats were divided into three groups, with each group being fed with water, a commercial product (TSN), or AAC1 broth prepared according to this disclosure.

Mechanical stress was applied to each group and upper spinal cord tissues containing the spinal trigeminal nucleus (STN) samples were obtained and processed for immuno-staining. Prior to immunostaining, slides were placed at room temperature and covered with 1×PBS for 5 minutes. PBS was removed, and liquid was replaced with a 5% normal donkey serum 0.1% triton solution for 20 minutes. Tissues were then washed with 5 mL 1×PBS. Working dilutions of rabbit anti-rat PKA (BD Biosciences, San Jose, Calif.; 1:500) were made using 5% normal donkey serum. Primary antibodies were allowed to incubate on tissues (100 µl/tissue) for 3 hours at room temperature. Samples were then washed with 5 mL 0.1% Tween 20-PBS and 2 mL 1×PBS. Working dilutions of donkey anti-rabbit IgG Alexa 488® was made by diluting stock antibodies 1:200 in 1×PBS. Secondary antibodies were allowed to incubate on sample slide (100 µl/tissue) for 1 hour at room temperature while protected from light. Slides were again washed with 5 mL 0.1% Tween 20-PBS and 2 mL 1×PBS, and mounted for fluorescent analysis using Vectashield fluorescent mounting media containing the fluorescent dye DAPI. Slides were cover slipped, sealed using clear nail polish, and stored at 4° C. until microscopic images were collected.

A Zeiss Z1 imager with apotome was used to acquire 10× Z-Stacked images of the V3 areas of the trigeminal ganglia and medullary horn of the STN. Zen 2011 software was used to evenly balance the background of each image prior to analysis. Gray scale jpeg images were opened in ImageJ software, where 10 non-overlapping regions of interests (RIOs) with an area of equal size were placed in areas representative of protein expression in each image, and the integrated pixel densities were measured. Background intensities were also acquired through similar procedure, and averaged. The average background intensity acquired from each image was then subtracted from each integrated density values from areas of interest. Subtracted integrated densities were averaged and fold changes were calculated as the average change±SEM from TMD control levels. Statistical differences were determined using the Mann-Whitney U test in SPSS software, and were considered to be different when $p<0.05$.

Figure 4:
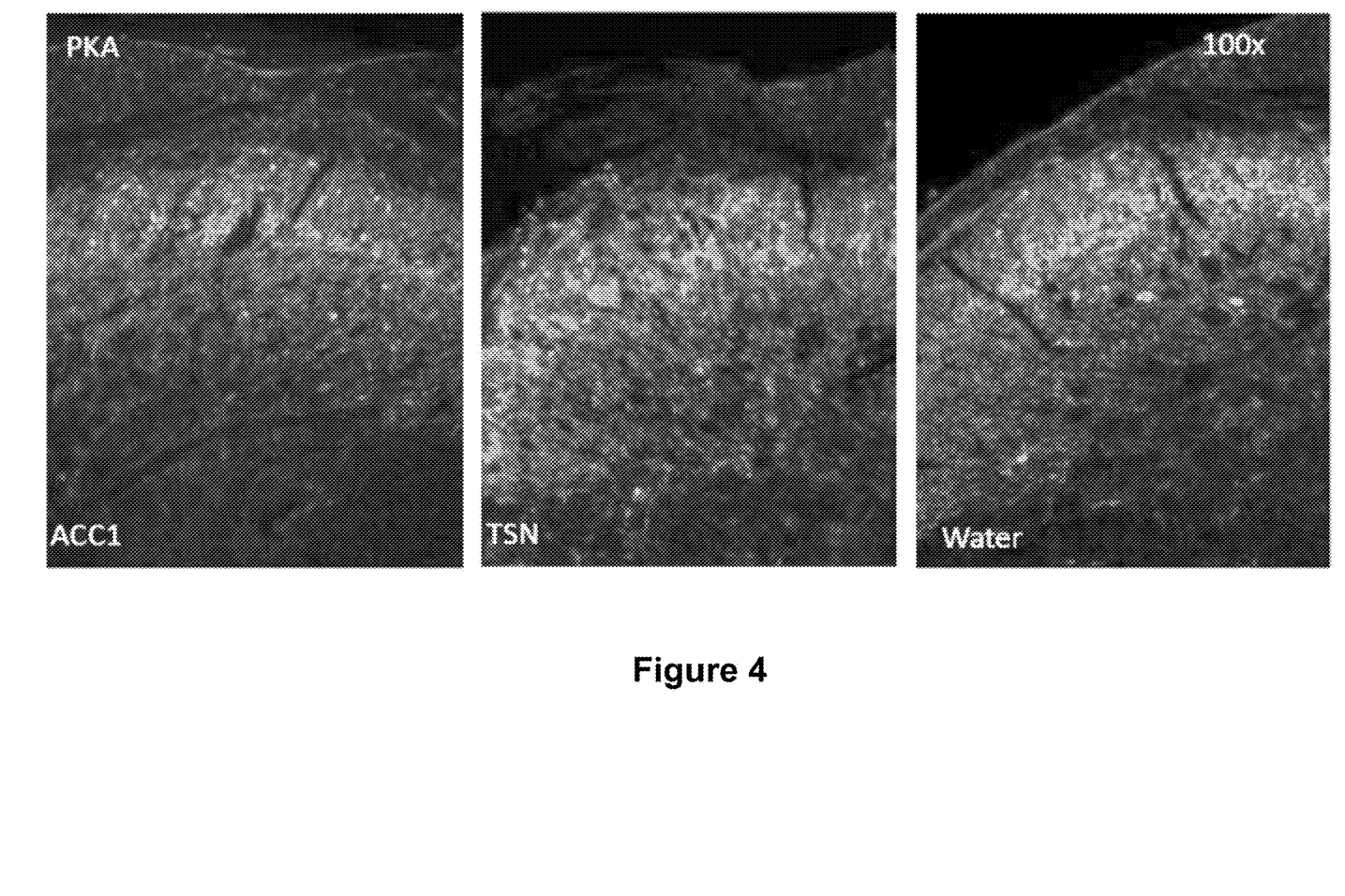
FIG. 4 shows that up-regulation of PKA is significantly repressed in animals fed with AAC1 broth as compared to animals fed with a commercially available product TSN.

The data in FIG. 4 provide evidence that elevated PKA levels caused by prolonged jaw opening are greatly repressed in AAC1 fed animals when compared to levels in animals consuming either water or a commercial product (TSN). In Table 6, the results of several experiments are summarized as the average fold change in the intensity of immunostaining when compared to water whose mean intensity was made equal to one.

TABLE 6

AAC1 repression of elevated PKA levels in response to jaw stress caused by prolonged jaw opening

| Broth | Average Fold Change | P Value (vs. TMD) | P Value (vs. TSN) |
|---|---|---|---|
| Water (TMD) | 1.00 ± 0.06 | 1.000 | 0.239 |
| AAC1 | 0.75 ± 0.02 | 0.001 | 0.000 |
| TSN | 0.94 ± 0.04 | 0.239 | 1.000 |

The AAC1 broth disclosed herein showed a greater ability to modulate the levels of PKA in the STN following joint stress when compared to a commercially available product. Based on the difference in composition of AAC1 and a homemade broth, we would predict that AAC1 would be significantly better at repressing stress-induced elevations in PKA levels in the STN.

Example 9 Nocifensive Responses of AAC1 as Compared to Other Broth Products

Temporomandibular Joint Disorder (TMD), is characterized by the continuation of pain behavior and sensation despite a decrease in nociceptive inputs (Herb et al., 2006). The increased sensitivity can be attributed to the development of a chronically sensitized state of the nerves that provide sensory innervation of the joint, muscles, ligaments, and tendons. TMD patients often report that their symptoms negatively affect other aspects of their life (Sessle, 2008). Some TMD patients develop protective behavior modifications that may limit or minimize their everyday activities. This protective behavior is termed "nocifensive" behavior. The objective of this study was to determine if AAC1 chicken broth could reduce TMJ stress-induced nocifensive behaviors in response to mechanical stimulation, and how its performance compares to homemade broth and commercially available products.

Three chicken broths (AAC1, TSN, and a home-style broth) were investigated in this study. Broth AAC1 (8% solids) was made at a 0.5% (w/v) while a homemade style broth (1.7%) was tested at a dose that would allow for an equal comparison of the ratio of percent solids between AAC1 and a homemade broth. Thus, the homemade broth was diluted 8 fold with filtered water by placing 62.5 mL of stock broth, and diluting the broth to 1 L. To test a competing commercially available broth at a similar concentration, a solution for TSN (33.3% solids) was made in a similar manner with the modification that the broth was allowed to warm until a consistency of the stock broth was non-gelatinous.

Broths were measured out into 16.7 g increments and placed into clean bottles as previously described. The bottle was then filled to the 1 L mark with filtered water. All solutions were then placed in a warm, sonication bath for 30 minutes to allow all components of the broths to evenly solubilize. Broths were placed in the refrigerator until they were administered to the animals via water bottle administration for 2 weeks prior to TMD induction.

Adult Sprague-Dawley male rats (200 g-300 g) were housed separately in clean, standard plastic rat cages (VWR, West Chester, Pa.) with non-restricted access to both food and water in a room with 12 hour/light dark cycles. Three consecutive days prior to testing, animals were allowed to enter the Ugo Basile Durham animal holding device (Ugo Basile, Collegeville, Pa.) for 5 min to acclimate to testing conditions. During this acclimation period, stimulation of hair follicles and epidermis located in the masseter and TMJ region of the face occurred by gently rubbing the area with a pipette tip. This stimulation was used to improve the condition of the animal to the testing procedure, thus reducing the number of false reactions to testing filaments. Baseline nocifensive behaviors were assessed by utilizing a modified version of the well-established von Frey method. A series of calibrated von Frey filaments were applied in increasing force to the cutaneous area over the masseter muscle. Prior to application, the muscle was palpated with the tip of the testing filament to insure proper placement. Once placement was established, a scientist blinded to the experimental conditions placed enough force on the location to accomplish a bend in the filament. Reactions observed after initiation of force to the area and prior to the bend of the filament, were verified by one other scientist and recorded. Each filament was applied 5 times, and recorded as the number of reactions obtained from 5 applications of each specific calibrated filament. Measurements were collected over both the right and left masseter muscles of each animal, which were averaged together to obtain a combined average number of reactions out of 5. Baseline readings were prior to 2 week feeding of all chicken broth products and again 24 hours prior to TMD induction.

Figure 5:
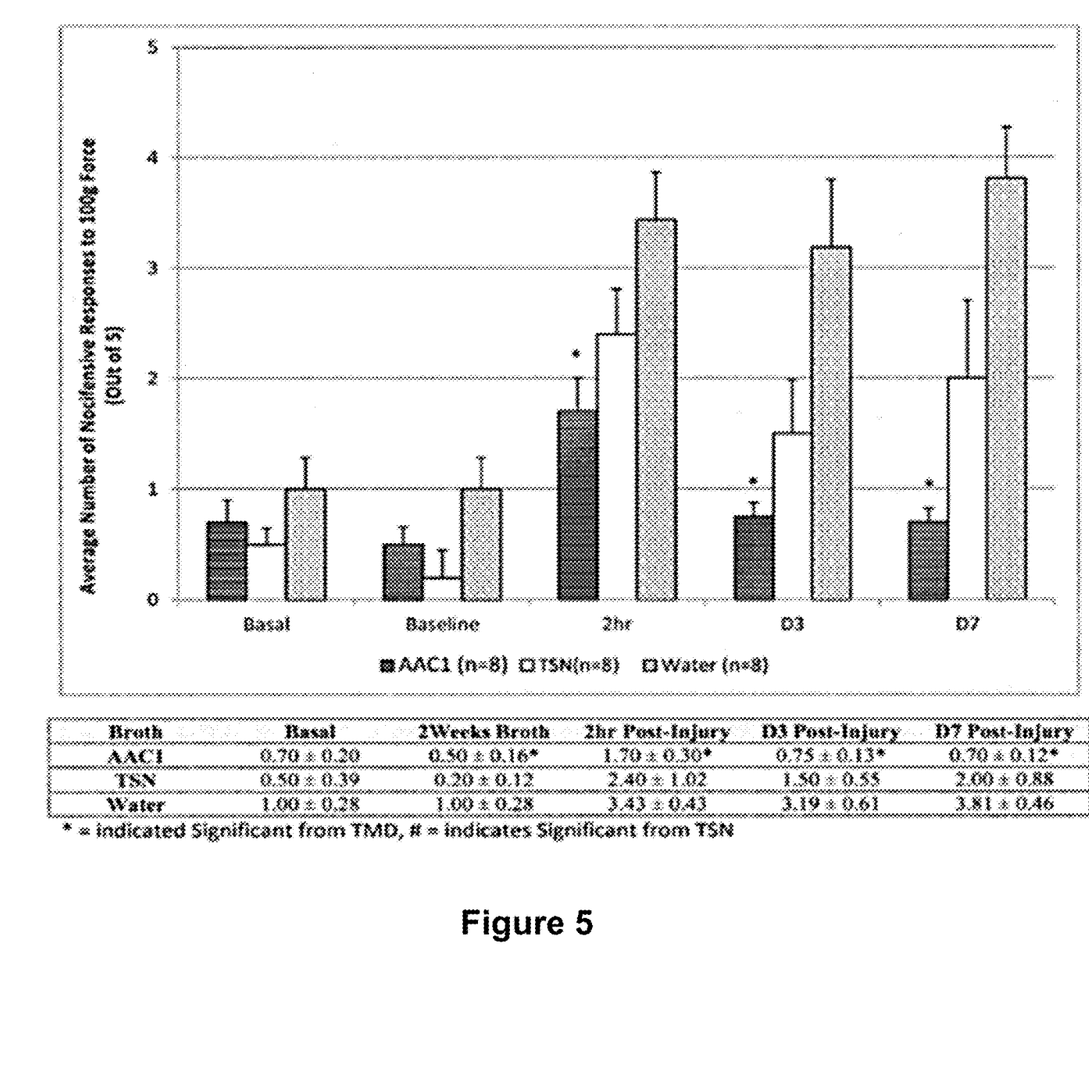
FIG. 5 shows nocifensive responses of AAC1 compared to a commercial product.

The number of nocifensive responses after 2 hr, 3 days, or 7 days in animals experiencing a mechanically induced TMD pathology was measured. The results of this study, which are shown in FIG. 5, demonstrate that AAC1 significantly reduces the number of nocifensive responses after 2 hr, 3 days, or 7 days in animals experiencing a mechanically induced TMD pathology. AAC1 significantly decreases the number of nocifensive responses as compared to TMD animals that consumed only water. The TSN product did not cause a decrease in nocifensive responses at any of the measured time points. Thus, while product AAC1 reduces nocifensive behaviors in animals experiencing chronic inflammation resulting from the prolonged jaw opening TMD model, this ability is not exhibited by a commercially available product. Based on results obtained from previous examples, as well as data presented in this example, we would predict that a homemade broth product would not significantly reduce TMJ stress induced nocifensive responses.

All animal studies described herein were performed using approved protocols in compliance with government rules and regulations. Changes may be made in the above methods and systems without departing from the scope hereof. It should thus be noted that the matter contained in the above description or shown in the accompanying drawings should be interpreted as illustrative and not in a limiting sense. The following claims are intended to cover generic and specific features described herein, as well as statements of the scope of the present method and system, which, as a matter of language, might be said to fall there between.

Although each of the embodiments described above has been illustrated with various components having particular respective orientations, it should be understood that the system and methods as described in the present disclosure may take on a variety of specific configurations with the various components being located in a variety of positions and mutual orientations and still remain within the spirit and scope of the present disclosure. Furthermore, suitable equivalents may be used in place of or in addition to the various components, the function and use of such substitute or additional components being held to be familiar to those skilled in the art and are therefore regarded as falling within the scope of the present disclosure. Therefore, the present examples are to be considered as illustrative and not restrictive, and the present disclosure is not to be limited to the details given herein but may be modified within the scope of the appended claims.

All references cited in this disclosure, including patents, patent applications, scientific papers and other publications, are hereby incorporated by reference into this application.

We claim:

1. A pharmaceutical composition comprising an effective amount of a broth prepared from poultry parts, said pharmaceutical composition comprising an enhanced quantity of chondroitin sulfate and having certain ratio between amino acids proline and histidine derived from said poultry parts, wherein the enhanced quantity of chondroitin sulfate derived from said poultry parts is at least 6% by weight of total dry solids of the pharmaceutical composition, and wherein said proline and histidine are present in said pharmaceutical composition at a ratio between proline and histidine of at least 4:1 by weight, and wherein said effective amount is an amount of the broth effective in treating a condition selected from the group consisting of joint pain and inflammation caused by the action of COX-2.

2. The pharmaceutical composition of claim 1, wherein said effective amount of the composition is an amount effective in reducing/alleviating joint pain.

3. The pharmaceutical composition of claim 1, wherein said effective amount of the composition is an amount effective in reducing COX-2 activity to treat inflammation caused by the action of COX-2 while not affecting activity of COX-1 in the individual.

4. A method of treating a condition in a subject, comprising administering to the subject an effective amount of a composition prepared from poultry parts, said composition comprising an enhanced quantity of chondroitin sulfate and having certain ratio between amino acids proline and histidine derived from said poultry parts, wherein the enhanced quantity of chondroitin sulfate derived from said poultry parts is at least 6% by weight of total dry solids of the pharmaceutical composition, and wherein said proline and histidine are present in said pharmaceutical composition at a ratio between proline and histidine of at least 4:1 by weight, and wherein said effective amount is an amount of the composition effective in treating the condition, said condition being selected from the group consisting of joint pain and inflammation caused by the action of COX-2.

5. The method of claim 4, wherein said effective amount of the composition is an amount effective in reducing/alleviating joint pain in the subject.

6. The method of claim 4, wherein said effective amount of the composition is an amount effective in reducing COX-2 activity to treat inflammation caused by the action of COX-2 while not affecting activity of COX-1 in the individual.

7. The method of claim 4, wherein at least 1 mg of said composition per pound of body weight of the subject is administered to the subject per day.

8. The method of claim 4, wherein between 1-100 mg of said composition per pound of body weight of the subject is administered to the subject per day.

9. The method of claim 4, wherein said composition is administered to the subject in a form selected from the group consisting of a medicament, a pharmaceutical composition, a food, a food ingredient, a supplement, and a nutraceutical ingredient.

* * * * *